(12) United States Patent
Kohl et al.

(10) Patent No.: US 9,387,064 B2
(45) Date of Patent: Jul. 12, 2016

(54) VALVULOTOME GUIDED BY A GUIDE WIRE/CATHETER

(75) Inventors: Gunter Kohl, Koblenz (DE); Heinz Schade, Reutlingen (DE); Matthias Tenholt, Mannheim (DE); Stefan Kennel, Mannheim (DE)

(73) Assignee: Andramed GmbH, Reutlingen (DE)

( * ) Notice: Subject to any disclaimer, the term of this patent is extended or adjusted under 35 U.S.C. 154(b) by 613 days.

(21) Appl. No.: 13/581,659

(22) PCT Filed: Mar. 1, 2011

(86) PCT No.: PCT/EP2011/000981
§ 371 (c)(1),
(2), (4) Date: Jan. 16, 2013

(87) PCT Pub. No.: WO2011/107249
PCT Pub. Date: Sep. 9, 2011

(65) Prior Publication Data
US 2013/0116500 A1    May 9, 2013

(30) Foreign Application Priority Data

Mar. 1, 2010  (DE) .......................... 10 2010 009 723

(51) Int. Cl.
*A61B 17/22* (2006.01)
*A61F 2/06* (2013.01)
*A61B 17/3207* (2006.01)

(52) U.S. Cl.
CPC ................. *A61F 2/062* (2013.01); *A61B 17/22* (2013.01); *A61B 17/320725* (2013.01); *A61B 17/32075* (2013.01); *A61B 2017/22038* (2013.01); *A61B 2017/22097* (2013.01)

(58) Field of Classification Search
CPC .................... A61B 17/221; A61B 17/320725; A61B 2017/22038; A61B 2017/22097
See application file for complete search history.

(56) References Cited

U.S. PATENT DOCUMENTS

| | | | | |
|---|---|---|---|---|
| 5,178,625 A | * | 1/1993 | Groshong | ...................... 606/159 |
| 6,565,588 B1 | * | 5/2003 | Clement | ........ A61B 17/320758 604/22 |
| 7,291,146 B2 | * | 11/2007 | Steinke et al. | .................. 606/41 |

\* cited by examiner

*Primary Examiner* — Ashley Fishback
(74) *Attorney, Agent, or Firm* — Berliner Steffin Azod LLP

(57) ABSTRACT

The invention relates to a valvulotome (1) guided by guidewire/catheter comprising
   a guidewire (2),
   a first inner tube (3) accommodating the guidewire (2),
   an expandable basket (5) with cutting elements (7), with said basket (5) being the distal end of a second tube (4) through which the first inner tube (3) extends,
   a catheter tube (8) through which the second inner tube (4) extends, said catheter tube being suited to accommodate and guide the expandable basket (5) in non-expanded state,
   a sleeve (6) that forms the distal end of the first tube (3) and functions as limiting element for the distal end of the basket (5) and through which the guidewire (2) has been passed.

10 Claims, 2 Drawing Sheets

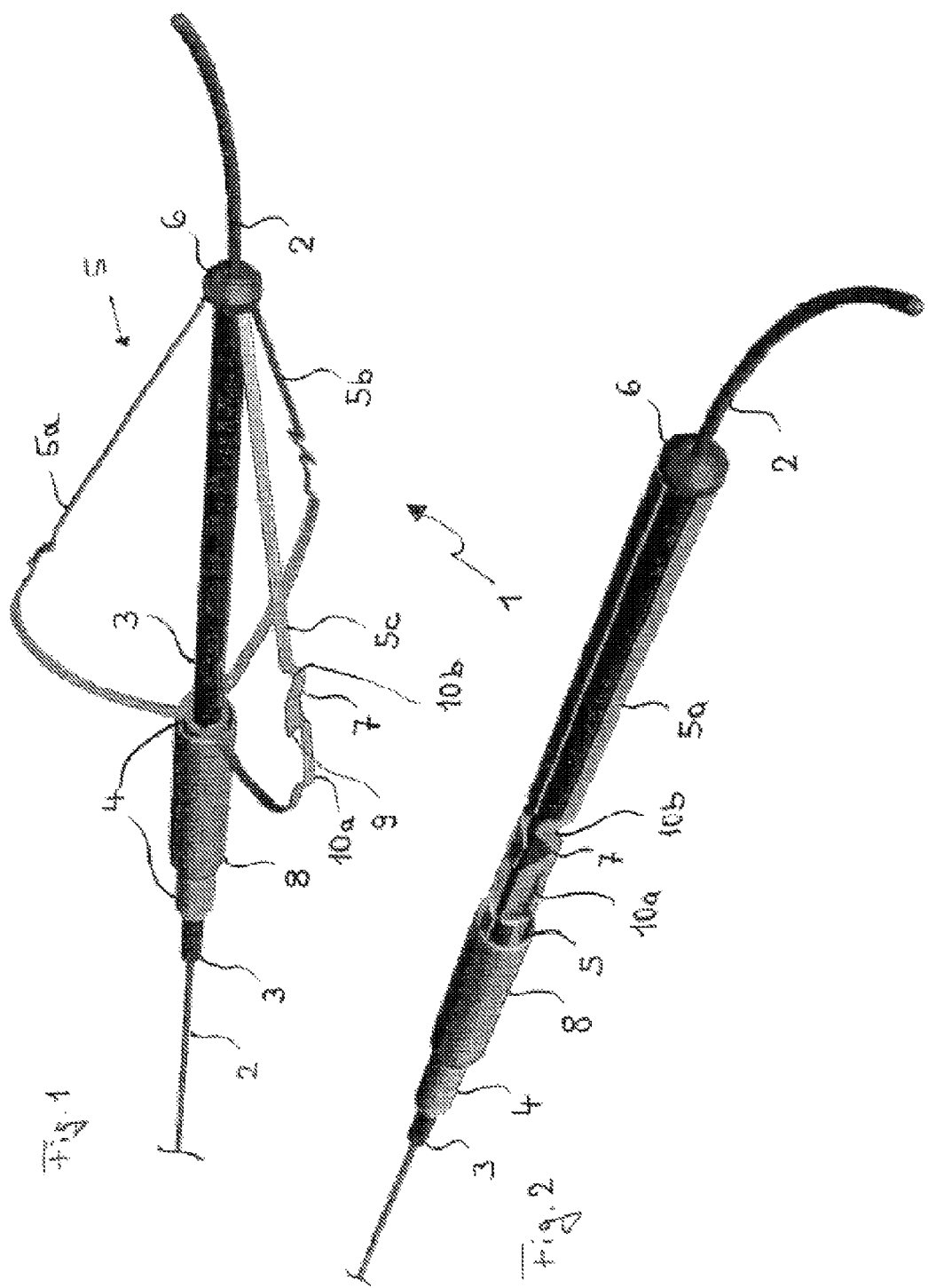

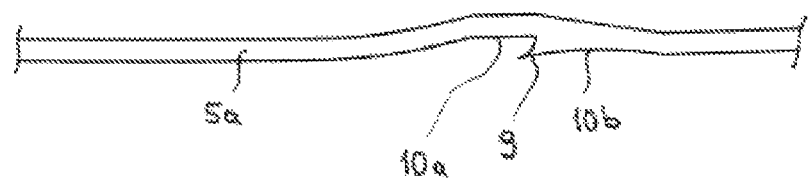
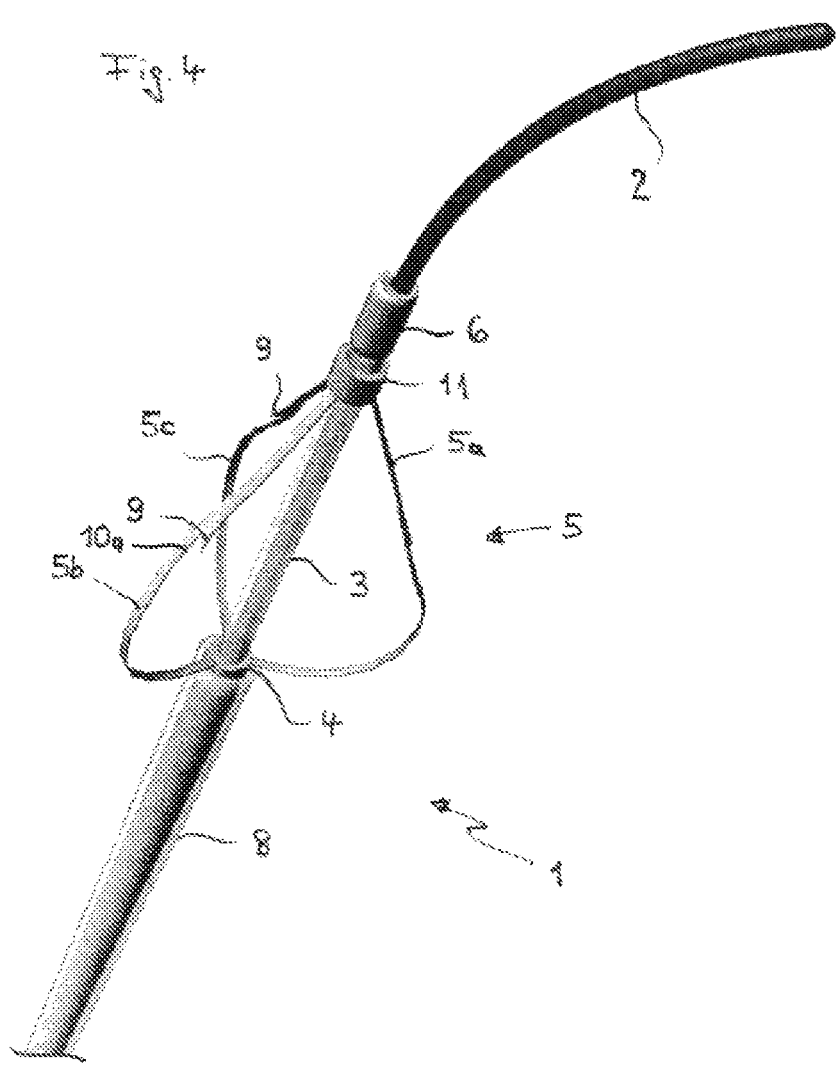

VALVULOTOME GUIDED BY A GUIDE WIRE/CATHETER

The invention relates to a guidewire/catheter guided valvulotome by means of which venous valves can be removed from a body vein intended for transplantation.

For the transplantation of body-own veins into the coronary region with a view to creating bypasses it is necessary to first remove venous valves from the veins to be used for this purpose. Venous valves are known to impair the flow of blood which is objectionable in the case of coronary arteries serving the supply of arterial blood to the myocardium. In this respect, body-own veins meant to create bypasses are as a rule taken from the thigh area of a patient and before grafting must be properly prepared. Provided there is sufficient time, such preparation of the vein usually takes place in the patient's body some time before the bypass operation is performed so that the relevant vessels are given sufficient time for recovery and healing.

For the purpose of removing venous valves in a patient's body so-called valvulotomes are employed which are endovascular instruments inserted into the respective vessel where they shear off the venous valves by means of laterally arranged cutting blades. Such an intervention is carried out, as a rule, with the help of a catheter inserted into the relevant vessel of the patient at the distal lower leg via the groin or through some other point of access, with a valvulotome, which is known per se, being subsequently transferred through this catheter to the desired application site. Having left the catheter the cutting elements of the valvulotome remove the venous valves which with the aid of a basket-like structure arranged near the tip of the valvulotome are then drawn into the catheter and taken out of the patient's body together with the catheter and valvulotome.

Such a valvulotome has been disclosed, for example, by publication WO 96/33662 A1 and is guided by a wire, equipped with a basket as well as cutting tools which are arranged in front of the basket. An atraumatic tip has been arranged distally.

This valvulotome is brought to the desired location by a catheter but its design lacks a controlling/steering function. In particular, this valvulotome has not been provided with a guidewire suitable for controlling or steering purposes. Moreover, the basket and cutting elements of this known valvulotome are arranged separately with the necessity that they must function in concurrence. Its cutting elements are movably arranged in a cutting head and pressed against the vessel wall by means of the basket which consists of spring elements.

Furthermore, other valvulotomes have been disclosed that essentially consist of a spring-type basket provided with cutting elements. A valvulotome of this type introduced and put into practice by the company of LeMaitre was also designed for guidance by catheter and had a basket with several braces into which cutting elements were integrated. However, these valvulotomes as well were incapable of being guided/steered independently.

Bearing this in mind, it is the object of the present invention to create a valvulotome capable of being guided independently to the desired application site by means of a guidewire. Moreover, the valvulotome should be controllable to such an extent that the cutting operation could be controlled by the attending physician and customized to suit the relevant diameter and condition of the patient's vein.

According to the invention this objective is achieved by providing a guidewire/catheter guided valvulotome comprising a guidewire, a first inner tube accommodating the guidewire (2), an expandable basket with cutting elements, with said basket (5) being the distal end of a second tube through which the first inner tube extends, a catheter tube through which the second inner tube extends, said catheter tube being suited to accommodate and guide the expandable basket in non-expanded state and a sleeve that forms the distal end of the first tube and functions as limiting element for the distal end of the basket and through which the guidewire has been passed.

The valvulotome according to the invention is guided in a customary catheter with which it interacts. It is provided with a guidewire extending over the entire length and projecting in the form of a curved tip at the distal end of the valvulotome. Making use of the guidewire the valvulotome can be guided to the application site in a precise manner.

The inventive valvulotome has also been provided with an inner tube through which the guidewire extends. Basically, this is to be viewed as a microcatheter which on the one hand accommodates and guides the guidewire and, secondly, also serves a function in the control of the valvulotome. Said inner tube may also be of wound design lending high flexibility, with the windings being coated and/or backed with a sheath of plastic material. Wound structures of this nature are known as spring-type guidewires with inner lumen.

The valvulotome according to the invention is furthermore provided with an expandable basket with cutting elements, with said basket being the distal end of a second tube through which the first inner tube extends. Expediently, the expandable basket with cutting elements is of one-piece design, i.e. cut from a suitable tube and shaped to suit its purpose. The basket is then attached to the distal end of the second tube, for example by means of adhesive bonding. Apart from the distal basket structure the second tube may be a suitably dimensioned catheter tube.

The inventive valvulotome is additionally provided with a catheter tube through which the second inner tube extends— and with it also the first inner tube as well as the guidewire— said catheter tube being suited to accommodate and guide the expandable basket in non-expanded state. When moved to its site of application the basket is thus retained in non-expanded state so that expansion does not take place before it has reached its destination site. In this manner it is ruled out the cutting elements may cause injuries while transfer takes place.

The valvulotome according to the invention is moreover provided with a sleeve that forms the distal end of the first tube and functions as limiting element for the distal end of the basket and through which the guidewire passes through a centrally located opening. The distal end of the basket may be movably arranged where it abuts against the sleeve which thus serves as stop element—or may be secured inside the sleeve.

Since the basket is of expandable design and thus has a variable diameter the attachment of the distal end of the basket inside the sleeve together with the distal end of the first tube enables both elements to be displaced against each other. Using the first inner tube causes the valvulotome to be retained in position whereas a movement of the second tube with distally arranged basket in longitudinal direction will bring about and can be employed for basket expansion or its elongation/stretching. In this way, the diameter of the basket can be expediently adjusted to suit the vessel diameter and the cutting elements optimally positioned, especially in the case of basket structures that are not of self-expanding design.

If the distal end of the basket is movable at the point where it touches the sleeve essentially the same considerations apply. The basket can be moved up to the sleeve which thus acts as stop element but on no account can be pushed beyond the sleeve. A certain small distance between the distal end of the basket and the sleeve is to be viewed as an advantage also because the basket when retracted back into the catheter tube is elongated and needs room to allow for such an increase in length. After all, the sleeve also serves as safety element preventing the basket from entering the vessel of a patient in the event the connection between the second middle tube and the basket structure becomes detached.

It needs not be specially emphasized here that all these elements—guidewire, first inner tube, second middle tube and the catheter tube—can be moved in relation to each other within predetermined limits.

It also goes without saying that the term "distal" as used here refers to the end of the valvulotome, catheter or guidewire facing away from the attending physician.

When transported to the destined site the inventive valvulotome with basket is positioned inside the catheter, i.e. the basket is in elongated/stretched form. Upon release from the catheter the basket may either be folded out or expands automatically, depending on material or configuration used.

The basket is provided with several braces on which the cutting elements are arranged. Preferably, more than two and in particular three braces are provided as in this way the valvulotome will be able to center itself within the vessel.

Distally, the braces are preferably brought together and secured in the sleeve, for example by welding. The braces may either be secured individually or jointly arranged in a short tubular section which is to be secured inside the sleeve. Apart from the option to attach the braces to the sleeve by welding they may as well be secured by crimping or adhesive bonding.

As proposed by the present invention the cutting elements are arranged on the basket. In case the basket comprises several braces the cutting elements are arranged on the braces. Preferably, these braces are provided with hook-shaped cutters pointing in proximal direction, said cutters extending along the plane of the braces. Said hook-shaped cutters are in particular arranged adjacent to offset portions of the braces so that the cutter faces, especially the cutting curvatures, are kept within the longitudinal extension of the braces. In the process of removing venous valves the valves are retained in the offset portion in front of the cutter and then severed by retracting the valvulotome.

Preferably, the guidewire is movable in respect of the inner tube which enables the valvulotome to be advanced sequentially. For this purpose, the guidewire is advanced to some extent with the remaining portion of the valvulotome suitably repositioned/followed up until the application site has been reached.

To be able to control the expansion of the basket respectively braces the second tube out of which the basket has been generated must in any case be kept movable in relation to the first inner tube, especially with basket structures that are not of self-expanding design. This enables the attending physician to spread the basket out by moving the second tube with respect to the first inner tube and in this way control the expansion of the basket. Having completed valvulotomy the basket can be brought into elongated form and together with the sleeve retracted into the catheter via the second tube. The guidewire can be retracted separately.

Fabricating the basket respectively braces and the second tube of a self-expanding material is considered expedient. For example, this material may be a spring steel, however expediently used is nitinol which is a material having shape-memory properties. A basket or braces made of nitinol may have such expansion characteristics impressed on so that the basket is caused to spread out automatically to the extent allowed by the respective vessel when being released from the catheter. As a result of the material's flexibility the basket can be retracted into the catheter after the treatment has been completed.

The valvulotome according to the invention can be provided with customary radiopaque marker elements which, in particular, may be arranged in the area of the sleeve and/or at the tip of the catheter. For example, also the sleeve may consist of radiopaque material.

Further elucidation of the invention is provided through the enclosed figures where FIG. 1: shows a valvulotome according to the invention with basket in expanded state;

FIG. 2: depicts the valvulotome as per FIG. 1 with the basket in retracted position;

FIG. 3: is a view of a brace with one cutting element and

FIG. 4 is another preferred variant of the valvulotome according to the invention.

The inventive valvulotome 1 as shown in FIG. 1 has a central guidewire 2 which extends through a first inner tube 3. At its distal end guidewire 2 has been provided with a curved tip which allows navigation within the vascular system.

The first inner tube 3 enables controlled movement of guidewire 2 and is also used as control element for basket 5 which as can be seen from the figure consists of three braces 5a, 5b and 5c. Starting point of basket 5 is the distal end of a second tube 4 to which it is attached by adhesive bonding. The braces 5a, 5b, 5c are made from a tube section consisting, for example, of nitinol, with the basket structure 5 being cut from this section with the help of a laser.

The distal end of the first inner tube 3 and the second tube with its braces 5a, 5b, 5c are secured within a sleeve 6. This sleeve 6 is to be viewed as the atraumatic tip of the valvulotome so that even when guidewire 2 is retracted the vessel walls are not exposed to hazards when in contact with the tip. Moreover, the sleeve also fulfills an essential function with respect to the maneuverability of basket 5.

In the figure braces 5a, 5b, 5c of basket 5 are shown in folded-out state, i.e. the basket has been expanded. In the event of self-expanding materials this folded-out state can be brought about through the pre-tensioning force, but with materials not having self-expanding properties this is achieved by moving the second tube 4 towards the sleeve and at the same time retracting the first inner tube 3.

In any case, movement in opposite direction always causes the basket structure 5 to be elongated so that it can be retracted into the surrounding catheter 8.

It is to be understood that catheter 8 as well as both tubes 3 and 4 and the guidewire are each led to the attending physician via a hemostasis valve which enables them to be controlled separately.

Basket 5 with braces 5a, 5b, 5c is provided with cutting elements 7 forming an integral portion of the braces and having hook-shaped cutters 9 pointing towards the proximal side. Cutting elements 7 extend along the plane of braces 5a, 5b, 5c. Due to the fact that braces 5a, 5b, 5c with their outer surface primarily extend parallelly to the vessel wall inadvertent injuries of the vessel wall through the blades are avoided. Hook-shaped cutters 9 are preferably arranged on braces 5a, 5b, 5c with offset portions 10a and 10b adjacent to them. This configuration enables a venous valve to be retained in the offset portion 10*a* located on the proximal side of cutter 9 and within this offset portion 10*a* moving said valve up to the cutting edge.

It is to be understood that also the second tube 4 with basket 5 and its elements may be fabricated of suitable plastic material featuring both appropriate stiffness and flexibility characteristics. In this case the cutters may be designed of a material having suitable edge retention properties.

In FIG. 2 the valvulotome depicted in FIG. 1 can be seen in partially retracted state. Identical reference signs are meant to refer to the same subject matter. Basket 5 of the valvulotome is partially located in catheter 8; the cutting elements 7 with offset portions 10*a* and 10*b* of brace 5*a* can be seen with the hook-shaped cutter being hidden as a result of the curvature. It is evident from the figure that braces 5*a*, 5*b*, 5*c* have been cut from a tube by means of a suitable cutting tool.

The situation shown in the figure illustrates the condition the inventive valvulotome is in immediately before the basket is moved out or, respectively, after the treatment has been performed and the basket retracted into the catheter and before the retracted catheter is removed from the body of the patient.

FIG. 3 shows a brace of basket 5 with cutter 9 having a cutting edge pointing to the proximal side and being arranged along the plane of brace 5*a*. Two offset portions 10*a* and 10*b* of the brace occupy a position on either side of the cutter 9.

FIG. 4 shows a preferred variant of a valvulotome according to the invention as illustrated in FIGS. 1 and 2. The braces 5*a* to 5*c* of this variant coincide with those shown in the sample depicted in FIG. 3. Incidentally, identical reference signs are meant to refer to the same subject matter.

The distal end 11 of basket 5 of the valvulotome shown in FIG. 4 is displaceable in respect of sleeve 6. Same as with the embodiment illustrated in FIG. 1 the basket 5 starts at the middle tube 4 and extends with three braces 5*a* to 5*c* to a tubular distal end 11 which can be moved against sleeve 6. In the case basket 5 consists of materials that are not self-expanding moving the basket 5 against sleeve 6 causes braces 5*a* to 5*c* to fold out/expand as a result of the pressure exerted. With a basket 5 made of a self-expanding material such as for example nitinol the length of the basket 5 increases when the basket is retracted necessitating a certain distance between the distal end 11 and sleeve 6 to allow room for this increase in length.

Moreover, braces 5*a* to 5*c* are provided with the cutters shown in FIG. 3 which are situated in the offset portions 10*a* and 10*b* of braces 5*a* to 5*c* and are arranged along the plane of braces 5*a* to 5*c*. In this arrangement the cutters 9 are essentially in alignment with the extension of braces 5*a* to 5*c* so that when the basket 5 is retraced into the catheter tube 8 the cutters do not interfere with or get caught up at the distal end of catheter tube 8.

The invention claimed is:

1. A valvulotome (1) guided by a guidewire/catheter comprising
   a guidewire (2);
   a first inner tube (3) accommodating the guidewire (2);
   an expandable basket (5) with cutting elements (7) the basket (5) comprising several braces (5*a*, 5*b*, 5*c*), said braces carrying the cutting elements (7), the cutting elements (7) being provided with hook-shaped cutters (9) pointing to a proximal side and extending along a plane of the braces (5*a*, 5*b*, 5*c*) in both an expanded and a non-expanded state of the expandable basket, wherein said basket (5) is a distal end of a second tube (4) through which the first inner tube (3) extends, the first inner tube (3) being slidably arranged in the second tube (4);
   a catheter tube (8) through which the second tube (4) extends, said catheter tube being suited to accommodate and guide the expandable basket (5) in the non-expanded state, the second tube (4) being slidably arranged in the catheter tube (8) and the expandable basket (5) being retractable in the non-expanded state into the catheter tube (8); and
   a sleeve (6) that forms a distal end of the first inner tube (3) and functions as a limiting element for a distal end of the basket (5) and through which the guidewire (2) has been passed, the valvulotome (1) being designed for removing venous valves in a vain of a patient.

2. The valvulotome according to claim 1, characterized in that the basket (5) comprises three braces (5*a*, 5*b*, 5*c*).

3. The valvulotome according to claim 1, characterized in that the braces (5*a*,5*b*,5*c*) are brought together distally in the sleeve (6).

4. The vaivulotome according to claim 1, characterized in that the hook-shaped cutters (9) are arranged on the braces (5*a*, 5*b*, 5*c*) with offset portions (10*a*, 10*b*) adjacent to them.

5. The valvulotome according to claim 1, characterized in that the guidewire (2) is movably guided with reset to the first inner tube (3).

6. The valvulotome according to claim 1, characterized that sleeve (6) is designed as an atraumatic tip.

7. The valvulotome according claim 1, charcterized that the basket (5) consists of as self-expanding material.

8. The valvulotome according to claim 7, characterized in that the self-expanding material is nitinol.

9. The valvulotome according to claim 1, characterized in that it has radiopaque marker elements arranged in the area of the sleeve (6) and/or the tip of catheter (8).

10. The valvulotome according to claim 9, characterized in that the sleeve(6) consists of a radiopaque material.

* * * * *